(12) United States Patent
Simakis

(10) Patent No.: US 9,878,442 B2
(45) Date of Patent: Jan. 30, 2018

(54) DEVICE, SYSTEM, AND METHOD FOR HOLDING ONE OR MORE STRUCTURAL LONG OBJECTS

(71) Applicant: Sam Simakis, Boulder, CO (US)

(72) Inventor: Sam Simakis, Boulder, CO (US)

(73) Assignee: Sam Simakis, Boulder, CO (US)

( * ) Notice: Subject to any disclaimer, the term of this patent is extended or adjusted under 35 U.S.C. 154(b) by 0 days.

(21) Appl. No.: 15/206,709

(22) Filed: Jul. 11, 2016

(65) Prior Publication Data

US 2016/0318661 A1 Nov. 3, 2016

Related U.S. Application Data

(63) Continuation-in-part of application No. 14/290,801, filed on May 29, 2014, now Pat. No. 9,416,804.

(Continued)

(51) Int. Cl.

| | |
|---|---|
| B25H 3/04 | (2006.01) |
| A45F 5/02 | (2006.01) |
| A45F 5/00 | (2006.01) |
| A63B 57/20 | (2015.01) |
| A01K 97/10 | (2006.01) |
| B43K 23/00 | (2006.01) |
| B25H 3/00 | (2006.01) |

(Continued)

(52) U.S. Cl.
CPC ............... *B25H 3/04* (2013.01); *A01K 97/10* (2013.01); *A45D 44/18* (2013.01); *A45F 5/00* (2013.01); *A45F 5/021* (2013.01); *A47B 81/005* (2013.01); *A47F 7/0028* (2013.01); *A47G 29/00* (2013.01); *A47K 1/09* (2013.01); *A61C 15/043* (2013.01); *A63B 57/203* (2015.10); *A63C 11/028* (2013.01); *B25H 3/006* (2013.01); *B43K 23/001* (2013.01); *B44D 3/123* (2013.01); *F16B 2/22* (2013.01)

(58) Field of Classification Search
CPC ......... A47L 13/512; B25H 3/04; A01K 97/08; A47K 1/09; A46B 17/00; A46B 17/02; A63B 57/203; F16B 2/22; F16M 13/02; A47G 29/00; A47G 29/08; A47F 7/0021; A47F 7/0028; B44D 3/123
USPC .......... 211/89.01, 62, 65, 68, 69, 69.1, 69.8, 211/70.5, 70.6, 70.7, 70.8; 248/110, 248/309.1, 311.2
See application file for complete search history.

(56) References Cited

U.S. PATENT DOCUMENTS

| | | | |
|---|---|---|---|
| 3,063,569 A | | 11/1962 | Huber |
| 3,365,761 A | * | 1/1968 | Kalvig .................. B25H 3/04 211/65 |

(Continued)

FOREIGN PATENT DOCUMENTS

| | | | | |
|---|---|---|---|---|
| DE | 3004312 A1 | * | 8/1981 | ............. A47G 29/08 |
| JP | 4521077 B2 | * | 8/2010 | ............. A47G 29/08 |

*Primary Examiner* — Ryan D Kwiecinski

(57) ABSTRACT

A device, system, and method for holding one or more structural long objects includes a plurality of adjacent flat membranes that are in direct contact with each other. The membranes have been slit to produce tabs that meet near a center of the membranes to hold the structural long object(s) more effectively than could be accomplished with a single flat membrane with tabs. The membranes are held in the body of the device or system by a retaining device located on one side of the membranes and a retaining feature of the body on the other side of the membranes.

13 Claims, 15 Drawing Sheets

Related U.S. Application Data

(60) Provisional application No. 61/829,600, filed on May 31, 2013.

(51) Int. Cl.

| | | |
|---|---|---|
| *A47G 29/00* | (2006.01) | |
| *A45D 44/18* | (2006.01) | |
| *B44D 3/12* | (2006.01) | |
| *A61C 15/04* | (2006.01) | |
| *A47F 7/00* | (2006.01) | |
| *A47B 81/00* | (2006.01) | |
| *F16B 2/22* | (2006.01) | |
| *A63C 11/02* | (2006.01) | |
| *A47K 1/09* | (2006.01) | |

(56) References Cited

U.S. PATENT DOCUMENTS

| | | | | |
|---|---|---|---|---|
| 3,375,934 A | * | 4/1968 | Bates | B01L 9/06 211/72 |
| 3,603,551 A | * | 9/1971 | Peterson | A47F 7/0028 211/70.6 |
| 4,138,055 A | * | 2/1979 | Harrison | B42D 17/00 232/1 C |
| 4,267,995 A | * | 5/1981 | McMillan | H02G 3/32 174/153 G |
| 4,325,484 A | | 4/1982 | Berry | |
| 4,334,621 A | * | 6/1982 | Weber | A47G 29/08 211/70.3 |
| 4,597,496 A | | 7/1986 | Kaplan | |
| 4,644,610 A | * | 2/1987 | Fish | A01G 13/04 211/70.6 |
| 4,995,509 A | | 2/1991 | Kornfeind | |
| 5,072,904 A | * | 12/1991 | Taylor | A46B 17/00 211/65 |
| D358,692 S | * | 5/1995 | Kasbohm | D34/10 |
| 5,450,970 A | | 9/1995 | Mitchell | |
| 5,678,348 A | * | 10/1997 | Zielinski | A01K 97/08 211/70.8 |
| 5,738,228 A | * | 4/1998 | Bittinger | A47F 7/0021 211/60.1 |
| D443,811 S | * | 6/2001 | Tisbo | D8/356 |
| 6,253,931 B1 | * | 7/2001 | Starkey | A47K 1/09 211/65 |
| 6,763,955 B2 | * | 7/2004 | Keis | A47J 47/16 211/60.1 |
| 6,932,223 B1 | * | 8/2005 | Lee | B25H 3/04 206/349 |
| 7,234,199 B2 | * | 6/2007 | Bushey | A47B 91/06 16/42 R |
| 8,931,242 B1 | * | 1/2015 | Sardo | B65B 51/04 383/121 |
| 9,380,860 B1 | * | 7/2016 | Taylor | A46B 17/06 |
| 9,416,804 B2 | * | 8/2016 | Simakis | F16B 2/22 |
| 2005/0276736 A1 | * | 12/2005 | Miller | A47K 1/09 422/300 |
| 2006/0011085 A1 | | 1/2006 | Whitley | |
| 2014/0034797 A1 | | 2/2014 | Terry Markwardt | |
| 2015/0060373 A1 | * | 3/2015 | Byeon | A46B 17/02 211/1.3 |

* cited by examiner

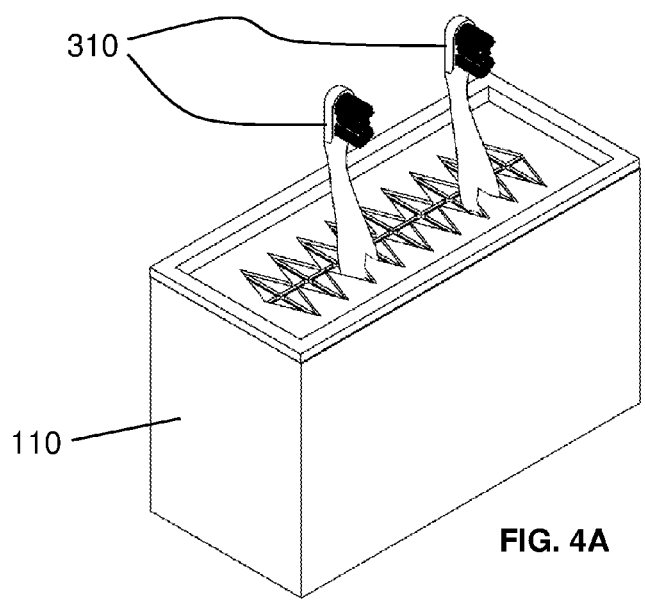
FIG. 4A
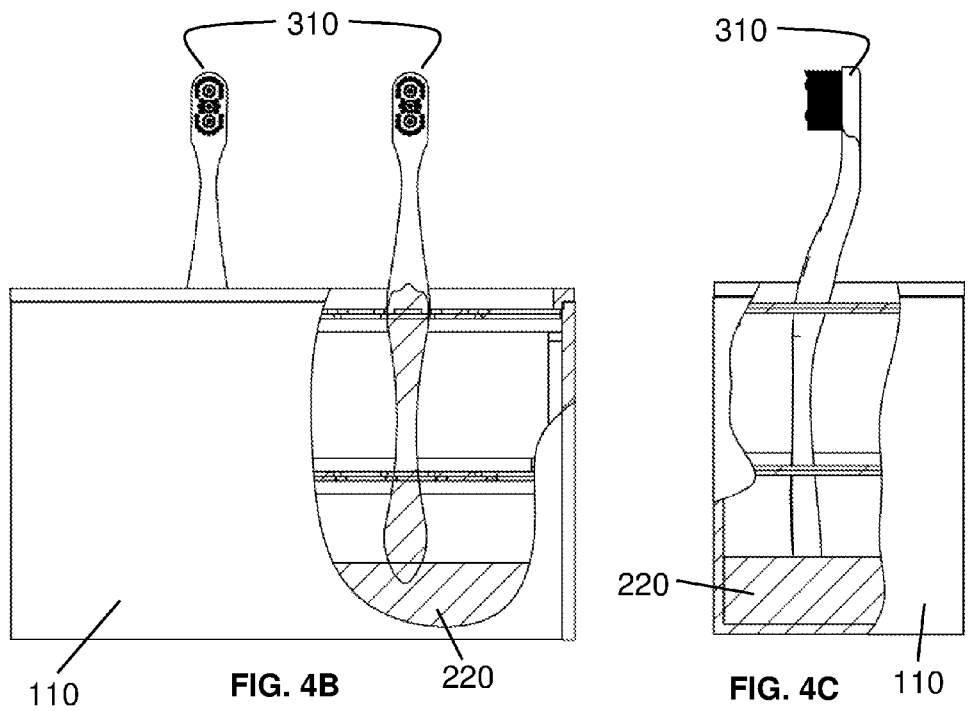
FIG. 4B  FIG. 4C

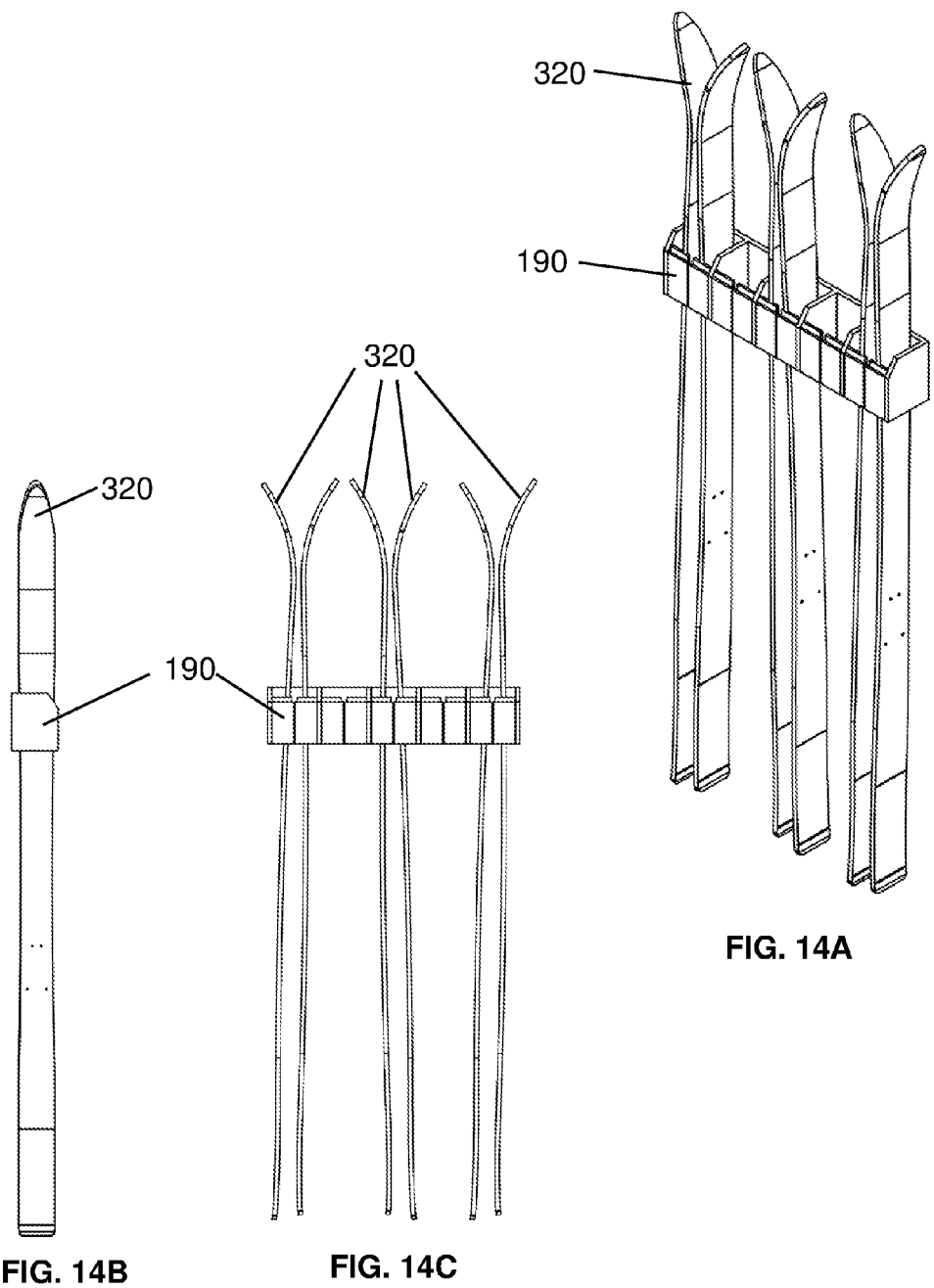

DEVICE, SYSTEM, AND METHOD FOR HOLDING ONE OR MORE STRUCTURAL LONG OBJECTS

CROSS REFERENCE TO RELATED APPLICATIONS

This application is a continuation-in-part of U.S. patent application Ser. No. 14/290,801 filed 29 May 2014, which claims the benefit of U.S. Provisional Patent Application No. 61/829,600 filed 31 May 2013, the entire disclosures of which are incorporated by reference herein.

BACKGROUND

The present invention relates generally to a holding device that uses a plurality of adjacent flexible diaphragms with deflectable tabs to secure, organize, and/or store objects that are (a) slender relative to their length and (b) sufficiently rigid to support themselves when the longest dimension is oriented vertically.

In many fields of use, the lack of an elegant solution for storing structural long objects (such as screwdrivers, toothbrushes, golf tees, writing implements, scissors, skis, and garden tools) can be a cause of frustration and inefficient work-practice. Some prior art holding devices use a single diaphragm mechanism with deflectable tabs that allow a portion of a structural long object to be inserted between the deflectable tabs. The use of a single diaphragm and set of tabs can result in tabs that are too flimsy, causing the object(s) to not be held securely enough, and/or tabs that are too stiff, making it difficult to insert or remove the object(s). Prior art single diaphragm based holding devices can also exhibit problems associated with of the size and thickness of the object they can effectively retain. These limitations occur at least partially due to properties (such as the stiffness) associated with the retaining material used. Some prior art holding devices utilize diaphragms manufactured from materials such as polyethylene, which can exhibit a Shore A Durometer hardness of greater than 90. As a result, the diaphragm may accept only a limited range of effective diameter objects without permanent deformation of the tabs.

Limitations of prior art holding devices can be addressed through the use of multiple adjacent diaphragms to double, triple etc. the number of tabs that engage a structural long object. Thus, even though the retaining force or resiliency of an individual tab of the softer and/or weaker diaphragm material is less than the retaining force of an individual tab of a prior art holding device that uses a single adjacent diaphragm, the increased number of tabs engaging an object allows the improved holding device to more securely retain objects of varying effective diameter, weights and flexibility. The use of multiple adjacent diaphragms that touch and engage one another can also facilitate the storage of multiple objects within the same compartment. Such a configuration can enable a more efficient usage of space. The plurality of adjacent diaphragms can allow for the use of softer diaphragm material. This softer diaphragm material can permit greater tab displacement. The greater tab displacement can allow a device to accommodate objects with larger effective diameter. The greater tab displacement can also permit the distal ends of the tabs of an improved holding device to meet or nearly meet each other in order to engage objects with smaller effective diameter. The configuration of the improved holding device can also be optimized by constructing different adjacent diaphragm layers from different materials that vary in characteristics (such as material properties, tab configurations, flexibilities, thicknesses, and/or surface properties).

Moreover, an improved device embodying principles of the invention can allow for the holding of fragile items without tearing or causing damage to fragile objects held by the device. The multiple adjacent diaphragms can multiply the strength of a holding device embodying principles of the invention. By incorporating softer materials and more diaphragms, an improved device can enable the storage of more fragile items, while minimizing the risk of tearing or wear on these items. The improved holding device could be placed on a horizontal surface, attached to a person's belt, attached to a wall, mounted in a vehicle, or placed and/or attached in any other configuration capable of being understood by anyone skilled in the art.

BRIEF DESCRIPTION OF THE DRAWINGS

For a more complete understanding of the present invention and the advantages thereof, reference is made to the following description taken in conjunction with the accompanying drawings in which like reference numerals indicate like features and wherein:

FIG. 4A shows the device of FIG. 2A being used as a toothbrush holder;

FIG. 4B is a front cutaway drawing of the toothbrush holder of FIG. 4A;

FIG. 4C is a side cutaway drawing of the toothbrush holder of FIG. 4A;

FIG. 14A shows the holder of FIG. 12A being used to hold skis;

FIG. 14B is a side view of the holder of FIG. 13A;

FIG. 14C is a front view of the holder of FIG. 13A;

Figure 1A:
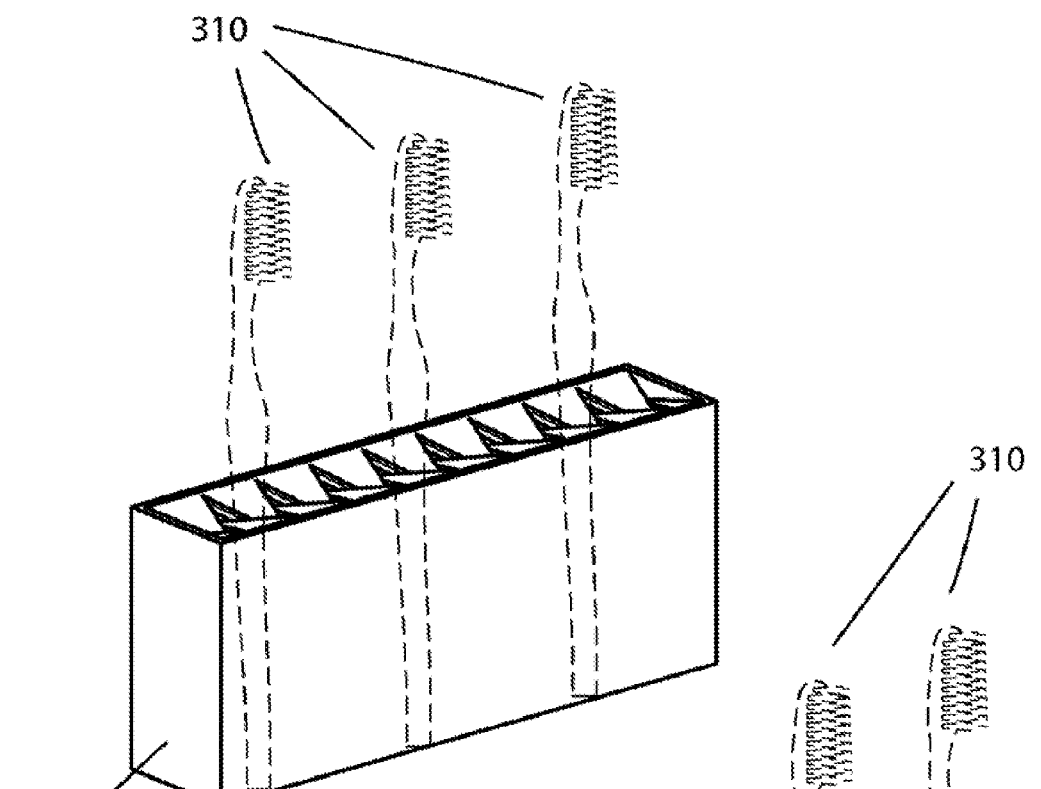
FIG. 1A shows an angular view of an embodiment of a holding device incorporating principles of the invention holding a plurality of structural long objects, in this example toothbrushes.

It should be understood that the drawings are not necessarily to scale. In certain instances, details that are not necessary for an understanding of the invention or that render other details difficult to perceive may have been omitted. It should be understood that the invention is not necessarily limited to the particular embodiments illustrated herein.

DETAILED DESCRIPTION

The ensuing description is presented for purposes of illustration and description and is not intended to limit the inventions to the forms disclosed herein. This description provides preferred exemplary embodiment(s) only, and is not intended to limit the scope, applicability or configuration of the disclosure. Rather, the ensuing description of embodiment(s) will provide those skilled in the art with an enabling description for implementing a preferred exemplary embodiment. Consequently, variations and modifications commensurate with the following teachings, and skill and knowledge of the relevant art, are within the scope of the presented inventions. The embodiments described herein are further intended to explain the best modes known of practicing the inventions and to enable others skilled in the art to utilize the inventions in such, or other embodiments and with various modifications and combinations of features and elements required by the particular application(s) or use(s) of the presented inventions.

It should be understood that various changes could be made in the function and arrangement of elements without departing from the spirit and scope as set forth in the appended claims. Preferred embodiments of the present invention are illustrated in the Figures, like numerals being used to refer to like and corresponding parts of the various drawings. Specific details are given in the following description to provide a thorough understanding of the embodiments. However, it will be understood by one of ordinary skill in the art that the embodiments may be practiced without these specific details.

In a preferred embodiment, the holder for structural long objects incorporates multiple adjacent slotted diaphragms designed to hold one or more structural long objects. As used herein the term structural long objects has specific meaning, in which:

"structural" refers to objects that maintain their intended manufactured form when fully supported with no external strain-inducing load (i.e. the objects are sufficiently rigid to support themselves when the longest dimension is oriented vertically); and "long objects" means objects that have a significantly greater length (longest dimension) than those dimensions that are perpendicular to this length (width and thickness). For purposes of this invention description and the appended claims a long object is one having a length at least four times greater than its width (where width is defined as a dimension perpendicular to the length throughout a majority of the length of the object) and at least four times greater than its thickness (where thickness is defined as a dimension orthogonal to the length and the width throughout at least a majority of the length).

Examples of objects that are structural long objects include, but are not limited to the following:

(a) Office items such as writing implements, scissors, and small tools, (b) Sports items such as skis, golf tees, and fishing poles;

(c) Tools such as paint brushes, screwdrivers, hammers, metal files, garden rakes, and brooms; and (d) Household items such as tooth brushes, dental flossers, cosmetic brushes, and kitchen utensils.

Figure 1B:
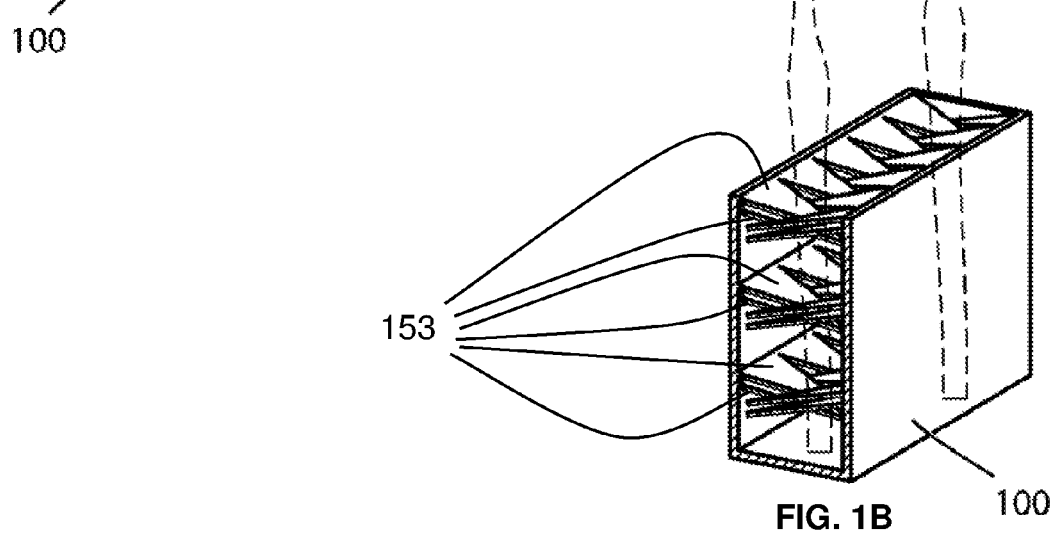
FIG. 1B shows an angular sectional view of the device of FIG. 1A.
Figure 2A:
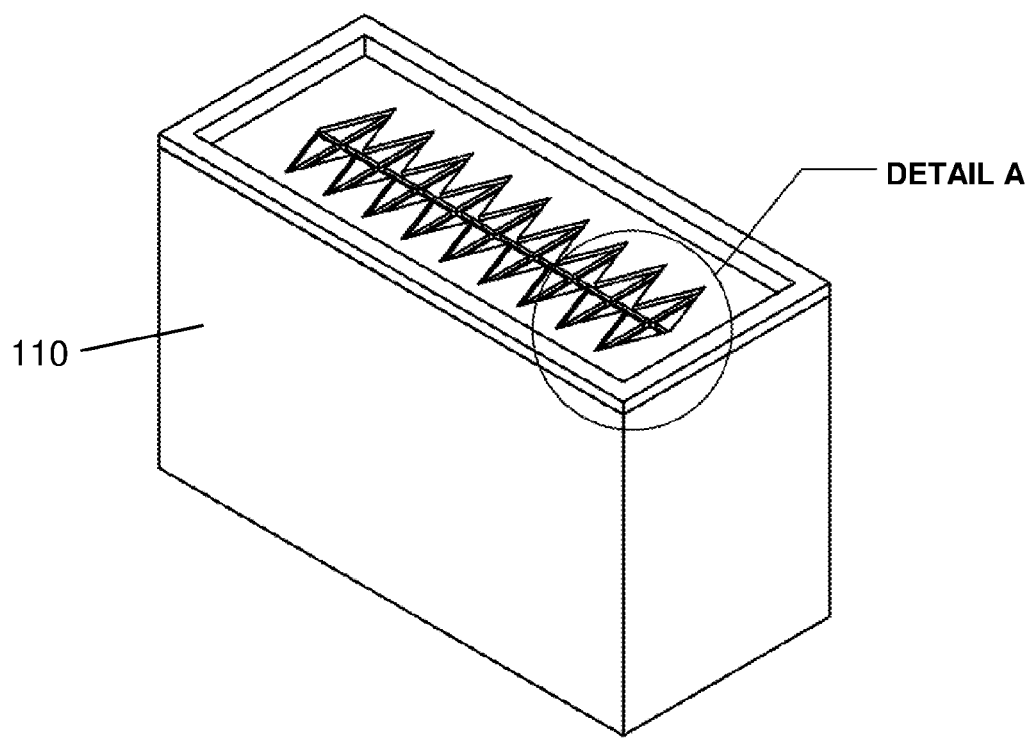
FIG. 2A shows a variation of the holder for structural long objects that was shown in FIG. 1A and FIG. 1B.
Figure 2B:
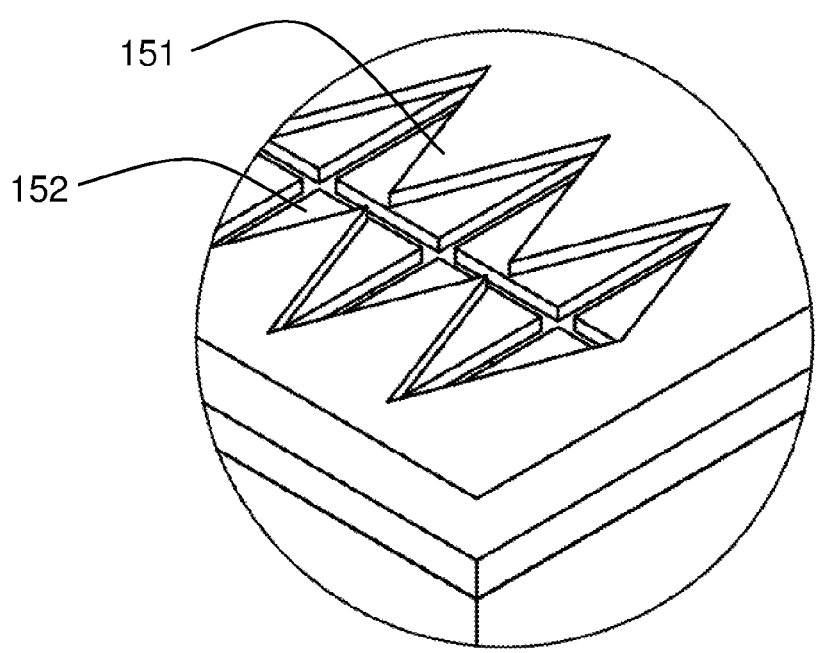
FIG. 2B shows detail A of FIG. 2A.

Reference will now be made to the accompanying drawings, which can assist in illustrating various pertinent features of the presented embodiments. FIG. 1A and FIG. 1B show an embodiment of a holding device 100 used for storing a plurality of toothbrushes 310. The holding device 100 comprises three pairs (stacks) of adjacent membranes or diaphragms 153, for a total of six diaphragms located in three diaphragm stacks. In this holding device 100, the diaphragms 153 have intersecting slits in a zigzag pattern, resulting in pointed opposing offset tabs. Each of the six diaphragms is identical.

FIG. 2A, FIG. 2B, FIG. 3, FIG. 4A, FIG. 4B, FIG. 4C, FIG. 5A, FIG. 5B, and FIG. 5C show a holding device 110 that is a variation of the holding device 100 of FIG. 1A and FIG. 1B. Both device 100 and device 110 are configured for holding structural long objects vertically. These devices can hold the objects in a configuration in which the objects do not touch each other when they are being held. The device 110 has two pairs of two adjacent membranes/diaphragms, for a total of four diaphragms located in two diaphragm stacks. The diaphragms or membranes are made from sheets of flat material. The adjacent diaphragms in each stack are in direct contact with each other. In holding device 110, each stack comprises two diaphragms 151 and 152 that are not the same. For example, diaphragm 151 has differently shaped tabs from diaphragm 152. The tabs in diaphragms 151 (the second diaphragms) are pointed and the points of the tabs having their bases at from opposite sides of the diaphragm 151 are aligned so the points meet at their distal ends along a center line that is parallel to the longest dimension of the diaphragm and centered in the diaphragm 151. The tabs in diaphragms 152 (the first diaphragms—i.e. adjacent to the lip in the housing) are blunt and rectangular. Opposite tabs in the first diaphragms, 152 are also aligned so that the slits separating the tabs having their points of attachment on one side are aligned with the slits separating the tabs having their points of attachment on the other side. In the first diaphragms 152 there is a central slit that is parallel to the longest dimension of the diaphragm that creates the opposing tabs. In devices that follow the principles of the present invention, adjacent diaphragms can be identical, they can share some similar characteristics, or they could be completely different from each other. The choice of the properties and characteristics of each diaphragm can be chosen to optimize the properties of a diaphragm stack. The differences between diaphragms in a stack could be any differences capable of being understood by anyone skilled in the art, including but not limited to:
  (a) Different materials;
  (b) Different diaphragm thicknesses;
  (c) Different slit configurations;
  (d) Different stiffnesses, which could be measured using a Shore Durometer test such as the ASTM (American Society for the Testing of Materials) D2240 type A scale; and
  (e) Different surface properties. For example, one diaphragm could have a very slipper surface and another diaphragm could have a stickier surface to help prevent a long structural object from sliding through.

Examples of materials and configurations that can be used for diaphragms (also called membranes) in embodiments of the present invention can include, but are not limited to elastomers (viscoelastic materials) such as:
  (a) Synthetic polymers;
  (b) Natural polymers such as natural polyisoprene (natural rubber);
  (c) Synthetic polyisoprene;
  (d) Polybutadiene (butadiene rubber);
  (e) Butyl rubber (copolymer of isobutylene and isoprene);
  (f) Styrene-butadiene copolymers;
  (g) Nitrile rubber (copolymer of butadiene and acrylonitrile);
  (h) EPDM (ethylene propylene diene rubber);
  (i) Epichlorohydrin rubber (ECO);
  (j) Polyacrylic rubber;
  (k) Silicone rubber;
  (l) Fluorosilicone rubber;
  (m) Fluoroelastomers;
  (n) Polyether block amides;
  (o) Polyethylene based elastomers;
  (p) Polypropylene based elastomers;
  (q) Vinyl-based elastomers;
  (r) Thermoplastic elastomers;
  (s) Polytetrafluoroethylene (Teflon) based elastomers;
  (t) Polysulfide-based elastomers; and
  (u) Chloroprene based elastomers, such as neoprene.

In one embodiment, the second diaphragm 151 comprises a 1/16-inch-thick layer of rubber and the first diaphragm 152 comprises a 1/16-inch-thick layer of neoprene. The rubber diaphragm 151 in this embodiment has a Shore A Durometer Hardness of between 40 and 50. The neoprene diaphragm 152 in this embodiment has a Shore A Durometer Hardness of between 40 and 50.

It should be noted that embodiments of the present invention can be made with any plurality of diaphragms. Although the figures show only two diaphragms in each stack, a diaphragm stack could also comprise three diaphragms, four diaphragms, five diaphragms, etc. There can be one diaphragm stack in an object holder, two diaphragm stacks, three diaphragm stacks, four diaphragm stacks, etc. The diaphragms can be thin. The diaphragms can be planar when in their rest states. The diaphragms can have a constant thickness in all regions except those that have been completely removed. Diaphragms in a stack can be parallel to each other. Diaphragm stacks can be parallel to each other.

The diaphragms shown in FIG. 2A, FIG. 2B, FIG. 3, FIG. 4A, FIG. 4B, FIG. 4C, FIG. 5A, FIG. 5B, and FIG. 5C are monolithic—each diaphragm in one layer of a diaphragm stack is made from a single piece of flat viscoelastic material that has been slit. Embodiments of the present invention can also comprise diaphragms that are made of multiple pieces of a flat material.

Figure 5A:
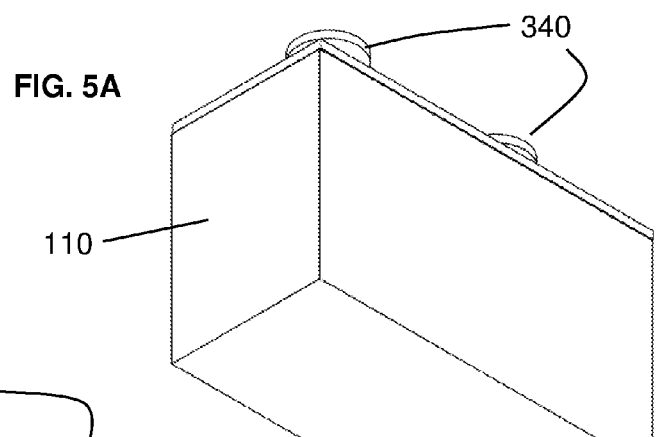
FIG. 5A shows an isometric view of the device of FIG. 2A being used as a golf tee holder.
Figure 5B:
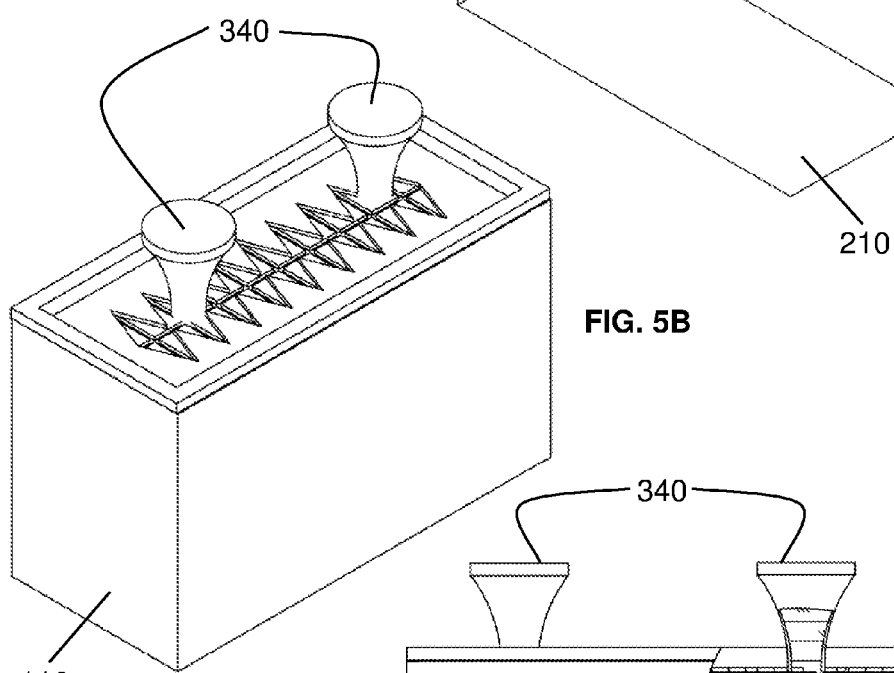
FIG. 5B shows another isometric view of the golf tee holder of FIG. 5A.
Figure 5C:
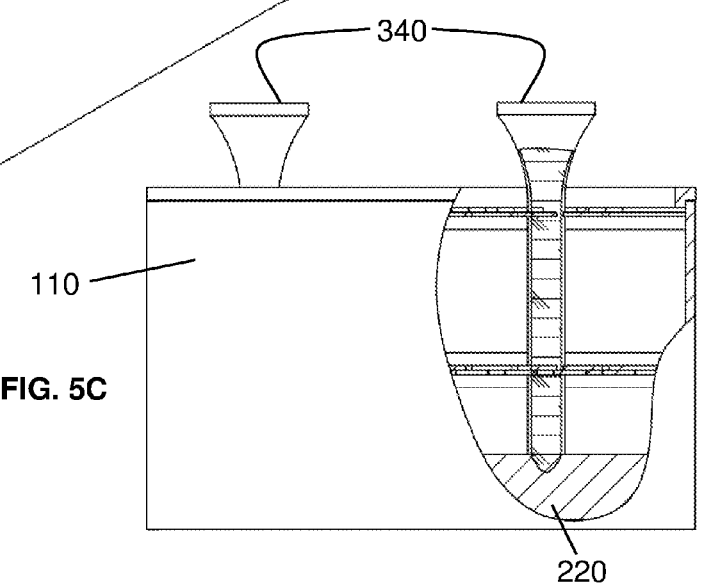
FIG. 5C is a front cutaway drawing of the golf tee holder of FIG. 5A.

FIG. 4A, FIG. 4B, and FIG. 4C show the object holder 110 being used for a household item, in this example toothbrushes 310. FIG. 5A, FIG. 5B, FIG. 5C show the object holder 110 being used for a sports item, in this case golf tees 340. As shown in FIG. 5A, the object holder 110 has a solid rigid bottom 210. As shown in FIG. 3, FIG. 4B, FIG. 4C and FIG. 5C, the object holder 110 can comprises a bottom pad 220. The bottom pad 220 can be made of any rigid or flexible material capable of being understood by anyone skilled in the art. In one embodiment, the bottom pad 220 is made of a flexible material configured to prevent the structural long object from moving laterally. Examples of materials that can be used for the bottom pad 220 can include an open cell foam and a closed cell foam. In one embodiment, the bottom pad 220 is an open cell foam that is ½ inch thick.

Figure 3:
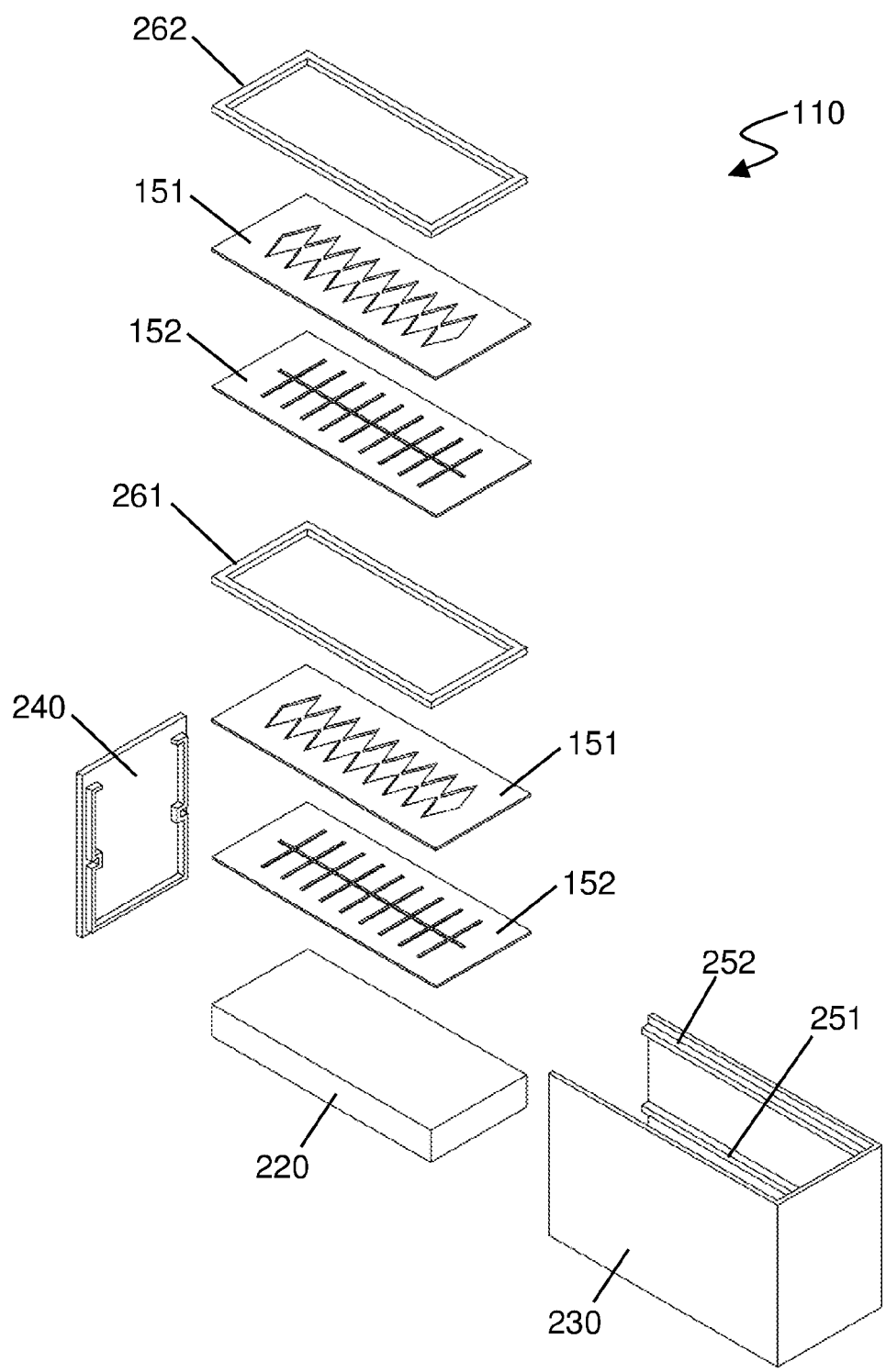
FIG. 3 shows an exploded view of FIG. 2A.

As shown in FIG. 3, the holder can comprise a holder body (or housing) 230 and an end cap 240. In one embodiment, the holder body 230 comprises a first diaphragm stack retaining feature 251 in the form of first lip (or shelf or rim) against which a first stack of diaphragms can rest and a second diaphragm stack retaining feature in the form of a second lip (or shelf) 252 against which a second stack of diaphragms can rest. In the embodiment shown in FIG. 3, the first adjacent pair (or stack) of membranes is held against the first lip 251 by a first retaining frame 261 and the second adjacent pair (or stack) of membranes is held against the second lip (or shelf or rim) 252 by the second retaining frame 262. The holder body 230 and end cap 240 can be made using any material and or manufacturing process capable of being understood by anyone skilled in the art, such as a plastic, and more specifically 3D printed ABS (acrylonitrile butadiene styrene) or injection-molded thermoplastic such as ABS (acrylonitrile butadiene styrene), polystyrene, polycarbonate, polyethylene, or polypropylene. In the embodiment shown in FIG. 3 the retaining frames 261 and 262, the diaphragms 151 and 152, and the bottom pad 220 are rectangular. It can be appreciated that frames, diaphragms, and pads used in embodiments of this invention can be any shape capable of being understood by anyone skilled in the art, including but not limited to circular, triangular, any quadrilateral, pentagonal, hexagonal, and octagonal.

Figure 6A:
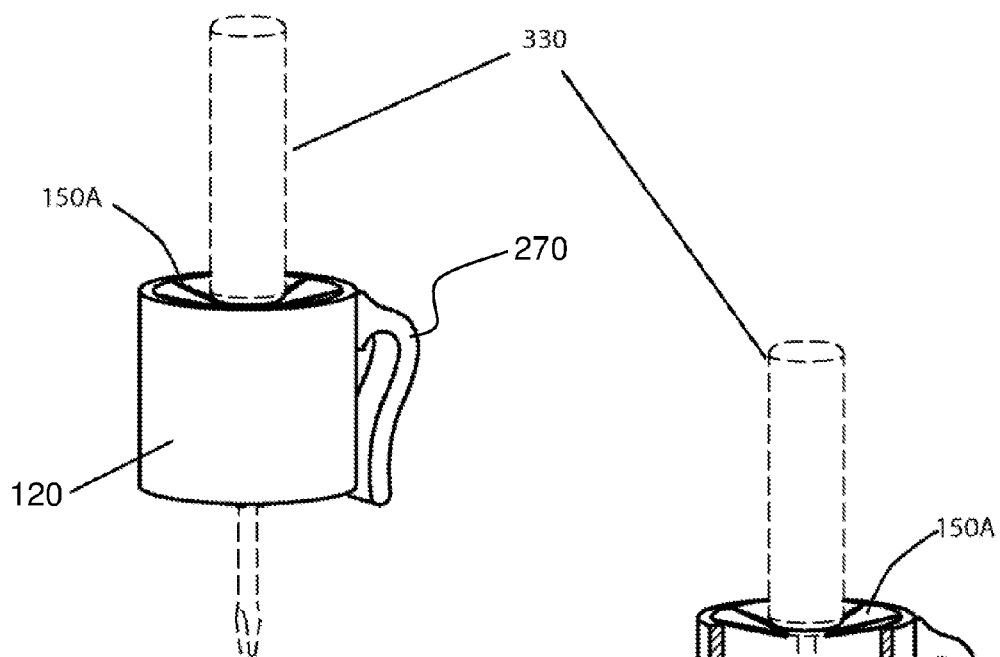
FIG. 6A shows a view of an alternate embodiment holding device being used to store a singular structural long object, in this example a screwdriver.
Figure 6B:
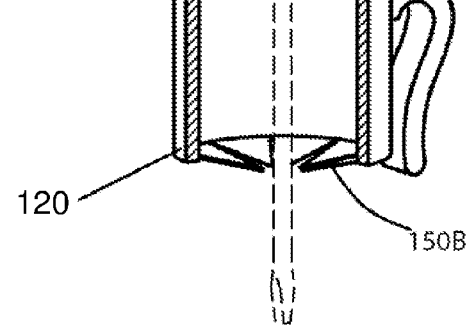
FIG. 6B is a sectional view of the embodiment of FIG. 6A.
Figure 7A:
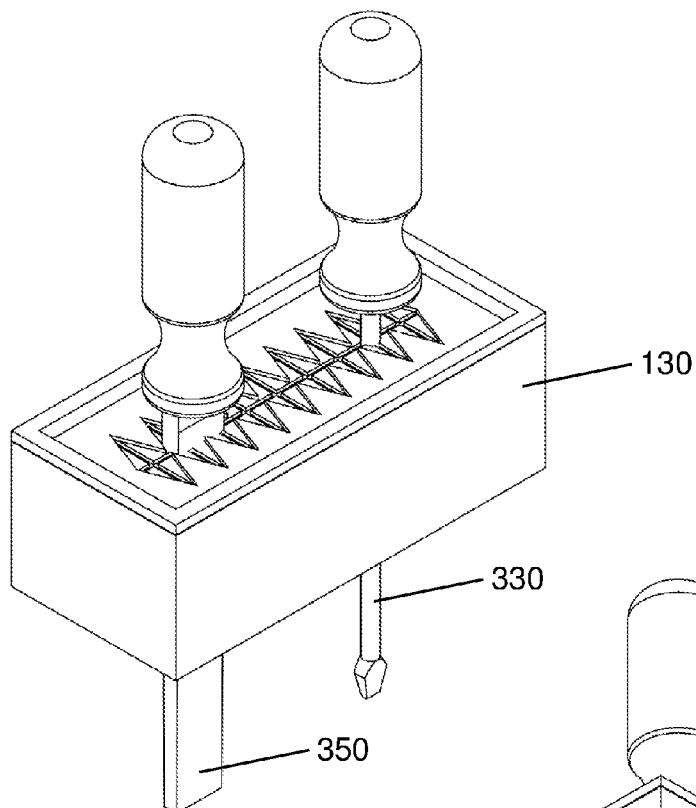
FIG. 7A shows another configuration of a holder for structural long objects.
Figure 7B:
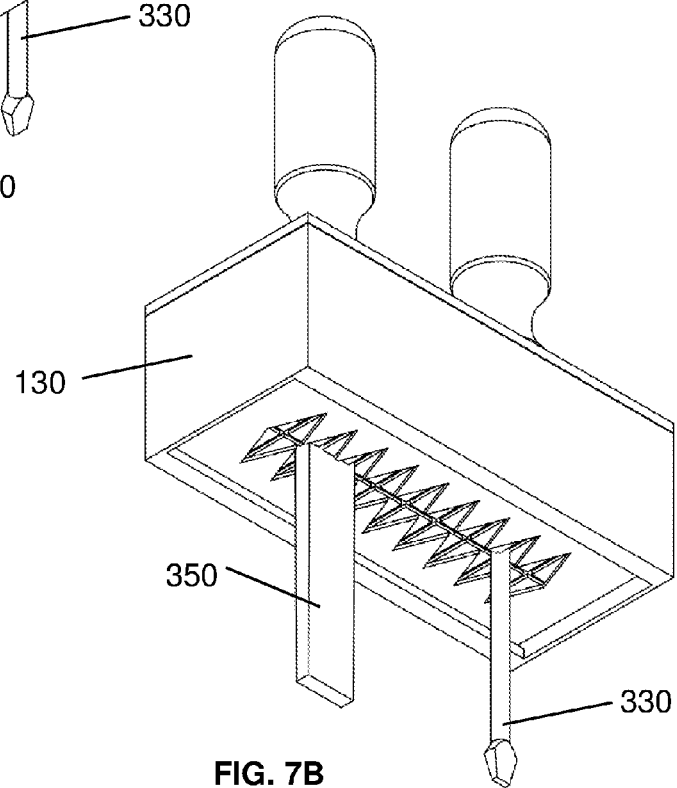
FIG. 7B shows another isometric view of the holder of FIG. 7A.

Referring to FIG. 6A and FIG. 6B, the principles of the present invention can be used to make a circular (or cylindrical) open bottom holding device such as that shown at 120. Referring to FIG. 7A and FIG. 7B, the principles of the present invention can also be used to make a rectangular open bottom holding device 130. By combining elements of holding device 120 with elements of holding device 110 that was shown in FIG. 2A, FIG. 2B, FIG. 3, FIG. 4A, FIG. 4B, FIG. 4C, FIG. 5A, FIG. 5B, and FIG. 5C, it is also easy to visualize how one could construct a circular closed bottom holding device for structural long objects.

FIG. 6A, FIG. 6B show that a user may displace one structural long object(s) such as a screwdriver 330 through the diaphragms 150A and 150B by grasping the object 330 at one end and pressing the opposite end through diaphragms 150A and 150B. It will be appreciated that in embodiments of the invention the varying designs of the device 120 (in FIG. 6A and FIG. 6B) and 130 (in FIG. 7A and FIG. 7B) can allow a user to at least partially insert structural long objects, such as the screwdriver 330 or metal file 350 through the diaphragms 150A and 150B using a single hand. The structural long objects can at least partially be inserted through multiple diaphragm stacks.

Diaphragms 150A and 150B in FIG. 6A and FIG. 6B are round and flat when in their rest states and that these diaphragms comprise slits that radiate inward from the periphery of the diaphragms 150A and 150B to create tabs having points that meet in the central axis of the holding device. The diaphragms 150A, 150B each includes a plurality of slits that extend there through. These slits define first and second sets pluralities of deflectable tabs. Each of the slits intersect at a center of its respective diaphragm, 150A and 150B. However, this is not a requirement. Although only one diaphragm 150A in the top stack and one diaphragm 150B in the bottom stack is shown in FIG. 6A and FIG. 6B, it can be appreciated that the cylindrically-shaped holder 120 can have multiple (two, three, four, etc.) diaphragms in the top stack and/or in the bottom stack and that there can be additional diaphragm stacks in the cylindrically-shaped holder that are located between the top stack and the bottom stack.

As a structural long object 330 passes through the diaphragm 150A, the tabs flex such that they are pushed inward into the recessed surface of the cylindrical housing of the circular holding device 120. Distal portions of at least a portion of the tabs engage the structural long object and work to maintain the object within the device. That is, the resiliency of the tabs provides a retaining force that securely holds the structural long object 330 within the holding device 120. However, by applying a sufficient pulling force, the tabs will release the object 330, in this example a screwdriver. Note that when the tabs deflect toward each other, the deflectable distal ends of the tabs in one diaphragm move in response to the movement of the deflectable distal ends of the other diaphragm when the tabs in the one diaphragm move in the direction of the other diaphragm.

Further referring to FIG. 6A and FIG. 6B, an attachment clip is shown at 270. Holding devices that use principles of this present invention can include such an attachment clip 270 and this clip can be configured for attachment to any item capable of being understood by anyone skilled in the art, including but not limited to a belt, an article of furniture such as a table or a desk, a wall, a door, a sports item such as a golf bag, and a part of the human body. The clip could attach to a flat object, such as a belt or an edge of a surface. The clip could attach to a cylindrical object, such as a broom or a flag pole. Attachment of the device can comprise a clip as is shown at 270 and this clip can use a spring or a feature of the holder that has springiness or flexibility. Embodiments of the present invention can be configured for attachment to another item through the use of things other than a clip such as mechanical fasteners (screws, bolts, nails, staples, hooks, fittings, and clamps), straps, and adhesives.

Figure 8A:
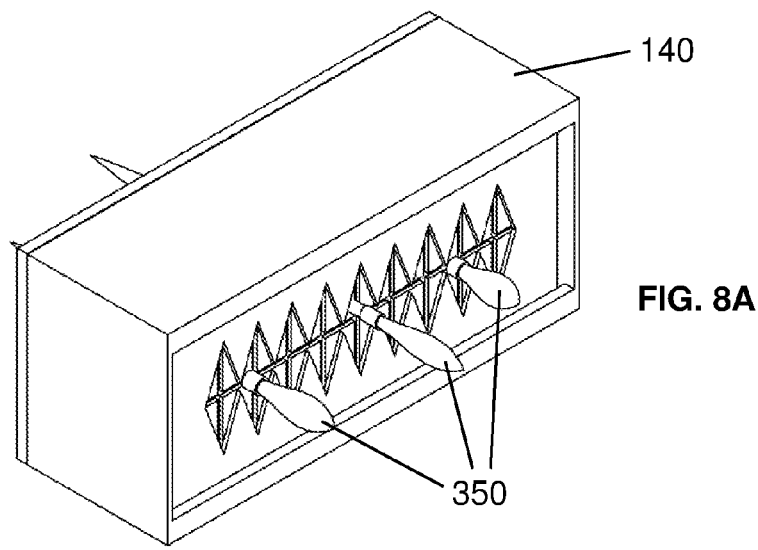
FIG. 8A shows the holder of FIG. 7A being used to horizontally store structural long objects.
Figure 8B:
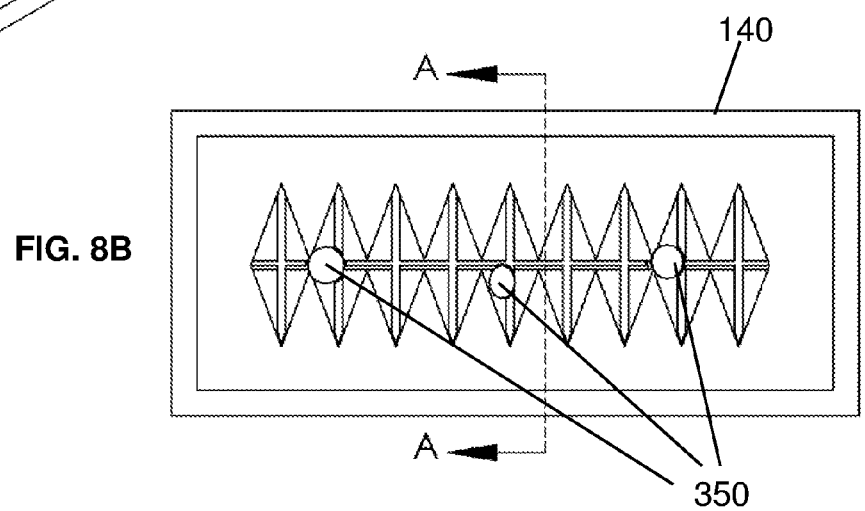
FIG. 8B shows a front view of the holder of FIG. 8A.
Figure 8C:
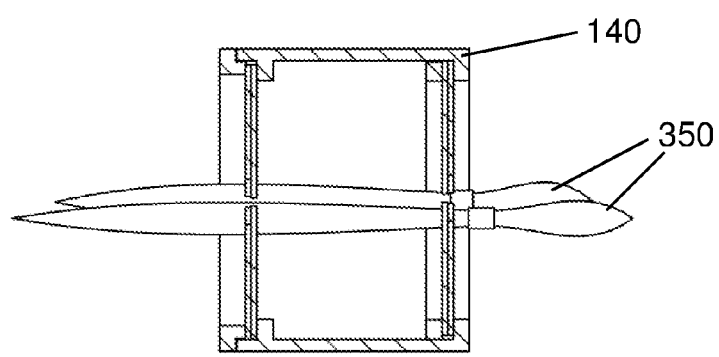
FIG. 8C shows section A-A of FIG. 8B.
Figure 9A:
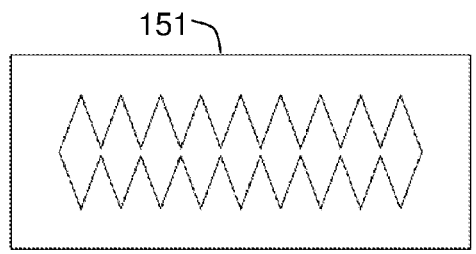
FIG. 9A shows a diaphragm with opposing pointed tabs.
Figure 9B:
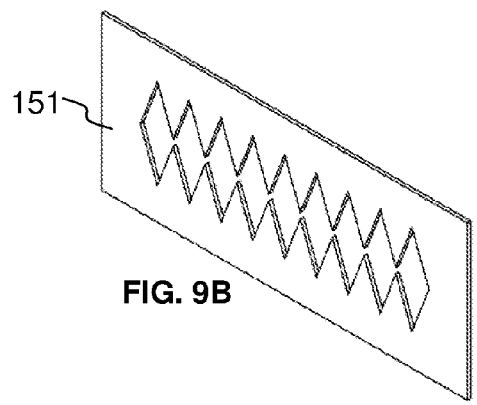
FIG. 9B is an isometric view of the diaphragm of FIG. 9A.
Figure 9C:
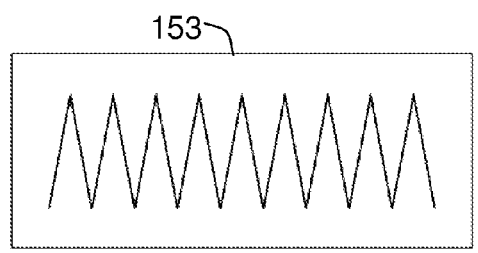
FIG. 9C shows a diaphragm with a saw tooth pattern of alternating tabs.
Figure 9D:
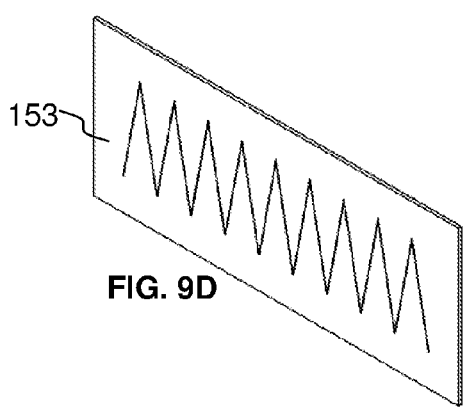
FIG. 9D is an isometric view of the diaphragm of FIG. 9C.
Figure 9E:
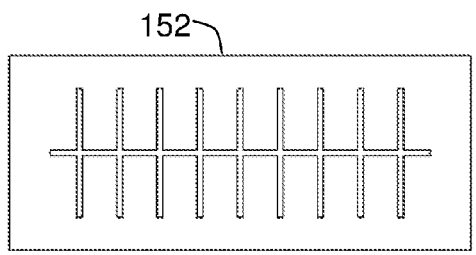
FIG. 9E shows a diaphragm with opposing rectangular tabs.
Figure 9F:
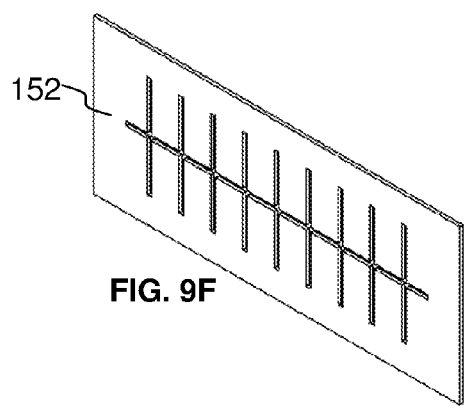
FIG. 9F is an isometric view of the diaphragm of FIG. 9E.

Referring to FIG. 8A, FIG. 8B, and FIG. 8C, embodiments of the present invention can also be oriented so that structural long object(s), such as paint brushes 350 are placed horizontally through multiple sets of adjacent diaphragms in a horizontally oriented open-ended holding device 140.

It can be appreciated that the diaphragms or membranes can have tabs shaped in any configuration capable of being created by anyone skilled in the art. Referring to FIG. 9A, FIG. 9B, FIG. 9C, FIG. 9D, FIG. 9E, and FIG. 9F:

The diaphragm or membrane can have pointed tabs with the points aligned 151;
The diaphragm or membrane can have pointed tabs with the points alternating such as the tabs produced by a single slit in a zigzag pattern 153; and/or
The diaphragm or membrane can have blunt and/or rectangular tabs 152.

The diaphragms shown in FIG. 9A, FIG. 9B, FIG. 9C, FIG. 9D, FIG. 9E, and FIG. 9F can be described as being comprised of tabs that are linearly aligned (i.e. in rows) and more specifically the tabs are in two opposing rows. Further variations of the shapes of the slits and tabs can include, but are not limited to:

(a) Tabs with rounded ends;
(b) Tabs that are in two aligned rows, but have gaps between them; and
(c) Tabs that have a combination of any of the features mentioned.

The individual diaphragms as presented may embody a contiguous membrane or a plurality of individual geometrically shaped tabs to comprise a full diaphragm. Note that at least some of the slits shown have at least one end that extends outward toward the periphery of the diaphragm.

Figure 10:
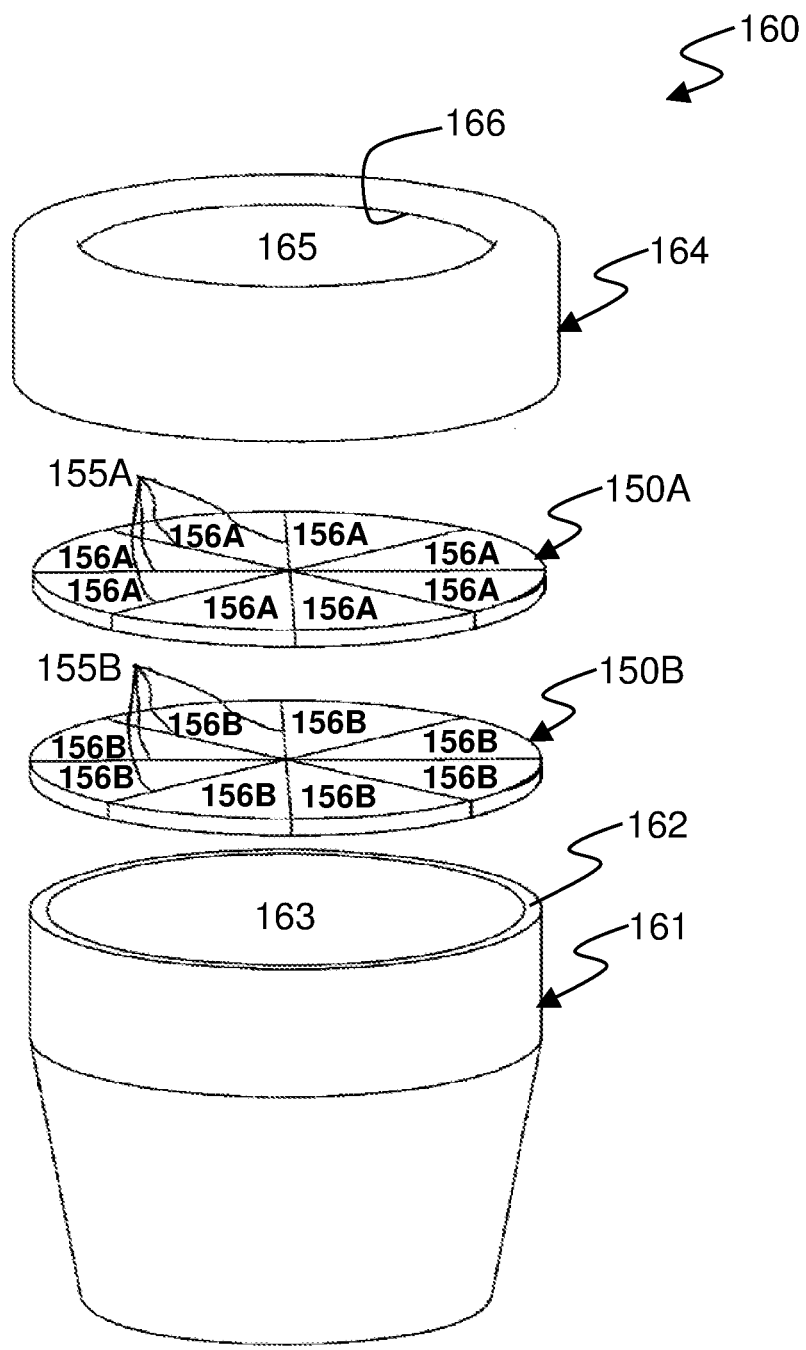
FIG. 10 shows an exploded view of a circular cup shaped (cylindrical) holder that employs principles of the present invention.

Referring to the exploded view of a cylindrical closed bottom holding device 160 shown in FIG. 10, the two diaphragms 150A, 150B are disposed adjacent to one another (e.g., stacked) on a lip (or shelf, or rim) 162 of a cylindrical housing (or holder body) 161. In this regard, the diaphragms 150A, 150B each extend over an aperture at an open end of the housing 161. Stated otherwise, the diaphragms extend over the recessed inside surface (or aperture) 163 of the housing 161 such that they may deflect inward when a structural long object is displaced through the center portions of the diaphragms. The peripheries of the diaphragms 150A, 150B are compressed against the lip (or rim) 162 of the housing 161 by an attachment element 164. In this case, the attachment element is retaining frame in the form of an annular retaining ring having a central aperture 165 that is disposed over the central portion of the diaphragms when the device is assembled. The retaining ring 164 has an inner wall 166 that is smaller than the inside diameter/cross-dimension of the rim (lip) 162 of the housing 161. Accordingly, when the retaining ring 164 is disposed onto the housing 161 the peripheries of the membranes 150A, 150B are compressed between the attachment element inner wall 166 and the housing lip 162 and thereby secured in place. An outer wall portion of the retaining ring 164 can engage an outside surface of the housing 161. The attachment element 164 may be connected to the housing 161 via a friction fit, adhesives, or mechanical fasteners, or any other fastening method capable of being understood by anyone skilled in the art.

In the embodiment shown in FIG. 10, the housing 161 is formed of generally circular and cylindrical cup having a closed bottom end. However, it will be appreciated that differently configured housings may be utilized. For instance, the housing may comprise any structure that allows for supporting the peripheries of multiple diaphragms such that tabs of the diaphragms may be deflected. Further, the housing need not be circular, cylindrical, and annular nor does it need to exhibit a contiguous perimeter. For example, the housing could be conical, the housing could be a frustum, the housing could be a cube, the housing could be rectangular, the housing could comprise a parallelogram, the housing could be triangular, pyramidal, four-side, five-sided, six-sided, etc. In this regard, will be appreciated that various different geometric shapes, open and closed may be utilized.

What is important is that the housing provide a structure that has an open aperture over which multiple diaphragms may be disposed.

As shown in the embodiment of FIG. 10, the diaphragms 150A and 150B are disposed adjacent (e.g., stacked) to each other. However, it will be appreciated that said diaphragms are not required to be stacked and may exhibit spacing between diaphragms. It will be further appreciated that in a configuration exhibiting a plurality of diaphragms in excess of two, the diaphragms need not exhibit equidistant spacing. Also shown in FIG. 10 is that the tabs 156A and 156B are formed from the slits 155A and 155B in a configuration where their distal ends each meet at the center of their respective diaphragms 150A and 150B and their other ends extend toward the peripheries of the diaphragms. It can be understood that other embodiments may be otherwise configured. For instance, each diaphragm may include a central aperture around which each of the slits radially extend from to define multiple tabs. However, it may be desirable that the distal tips of the tabs meet such that small diameter structural long objects may be held by the device. For instance, a single diaphragm prior holder intended to hold a pen of diameter 0.5" exhibiting a design of tabs 156A and 156B spaced from the center of the diaphragm creating an aperture 12 of size 0.3" is not able to securely retain an artist's paintbrush with diameter 0.125"

It has been recognized that utilization of multiple diaphragms allows for providing adequate retention force for maintaining an object within the holding device while allowing the use of softer materials to form the diaphragms. In this regard, softer diaphragms allow the device to hold objects with very small effective diameters as well as objects exhibiting larger effective diameters. The present inventor has discovered that devices known in the prior art are limited with regard to the size and thickness of objects that such devices can retain. These limitations occur at least partially due to properties associated with materials utilized in the construction of the diaphragm. Examples of limitations associated with prior art devices include the following. To hold objects with small effective diameter, the tabs 156A and 156B in FIG. 10, of such a diaphragm may need to meet nearly in the center of the diaphragm. The close spacing of the distal ends of such tabs limits the thickness of objects that may be displaced through the diaphragm. Use of a softer diaphragm material permits displacement of a thicker object through such a diaphragm but results in a reduced retention force applied by each tab. As used herein, "effective diameter" refers to the measurement across the widest portion of the object as inserted into the device. For a structural long object, this effective diameter can be defined as the square root of the sum of the squares of the width and the thickness of the object where length is defined as the longest dimension of the object, width is defined as a dimension perpendicular to the length throughout a majority of the length of the object, and thickness is defined as a dimension orthogonal to the length and the width throughout at least a majority of the length of the object.

Embodiments of the invention can address problems associated with size and thickness constraints associated with prior art devices. That is, rather than utilizing a stiffer plastic diaphragm, the diaphragms in a device incorporating embodiments of the invention are typically comprised of an elastomeric material that is considerably more pliable than most plastics. In this regard, it has been found by the inventor that materials having a Shore A Durometer hardness of less than 90 provide a suitable diaphragm for the holding device. Accordingly, use of lower Durometer materials, such as Shore A Durometer 90 and lower in a single diaphragm configuration can result in failure to retain structural long objects within the holding device. Therefore, to hold thicker structural long objects, prior art single adjacent diaphragm holding devices typically utilize tabs that have a gap between the tips of the tabs. As will be appreciated, if an object holder incorporates a gap between opposing tabs, it cannot hold structural long objects exhibiting a smaller effective diameter without design changes.

More specifically, materials having a Shore A durometer hardness of less than 90, more preferably less than 80 and yet more preferably less than about 70 provide diaphragms that allow deflection that is adequate to permit insertion of large effective diameter structural long objects while also permitting the engagement of small effective diameter structural long objects. In one particular embodiment, the device utilizes neoprene rubber diaphragms having a thickness of approximately 1/16 of an inch. In contrast, most plastics (e.g., polyethylene, polypropylene etc.) have a Durometer hardness considerably in excess of the claimed range. That is, many plastics are too hard to be measured utilizing the Shore A Durometer scale. For instance, most plastics have a minimum Shore D Durometer hardness of 55, which equates to a hardness that is greater than the maximum measure of Shore A Durometer hardness.

The use of the multiple diaphragms allows for providing sufficient retention force to maintain a thicker and/or heavier structural long object or objects object within the holding device. That is, even though each tab of the softer diaphragm material has a reduced resiliency, the increased number of tabs provided by the multiple diaphragms results in a holding device having sufficient retention force for as broad of a range of object shapes and sizes as possible. Further, the use of a softer diaphragm material reduces the potential of painful or injurious results to a user's finger that is inserted into the device. That is, prior art devices having hard plastic tabs can result in a situation where a user pushes their finger through the stiffer tabs, which pinch the finger upon removal. Utilization of the more easily deflectable tabs prevents such inconvenience for the user. That is, the pliability of the tab material permits removal of a user's finger without risk of injurious or painful use.

Figure 11A:
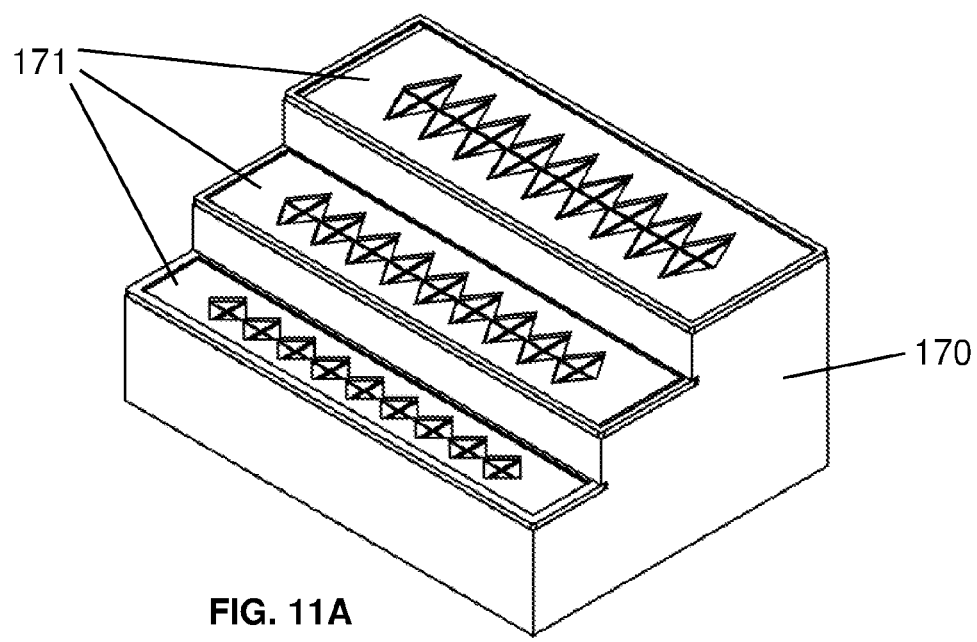
FIG. 11A shows a multi-tier holder for structural long objects.
Figure 11B:
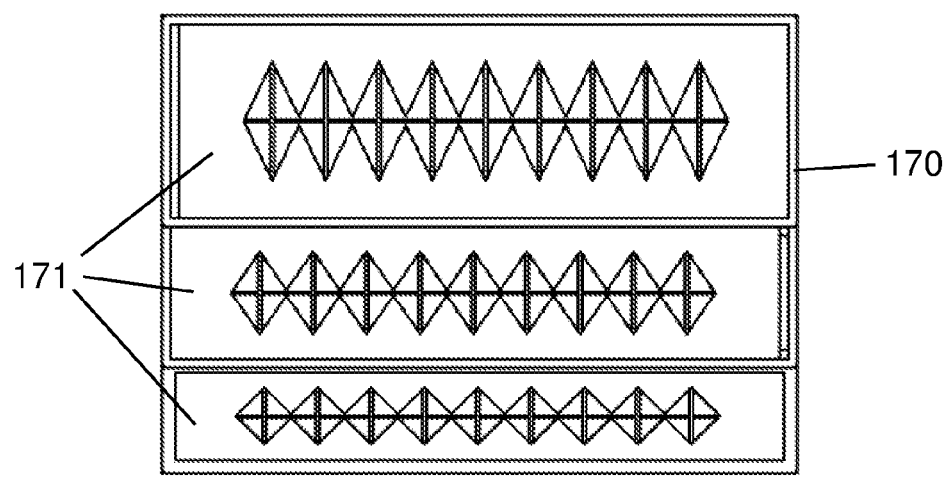
FIG. 11B is a top view of the multi-tier holder of FIG. 10A.

FIG. 11A and FIG. 11B show an embodiment of the present invention in the form of a multi-compartment holding device 170. In this case, each holding device compartment 171 can have its own pairs of adjacent diaphragms, similar to what was shown in other embodiments in this patent specification and figures. The diaphragms in this holding device 170 are perpendicular to the intended direction of insertion of the structural long objects and these diaphragms are configured for partial insertion of the structural long objects.

Figure 12:
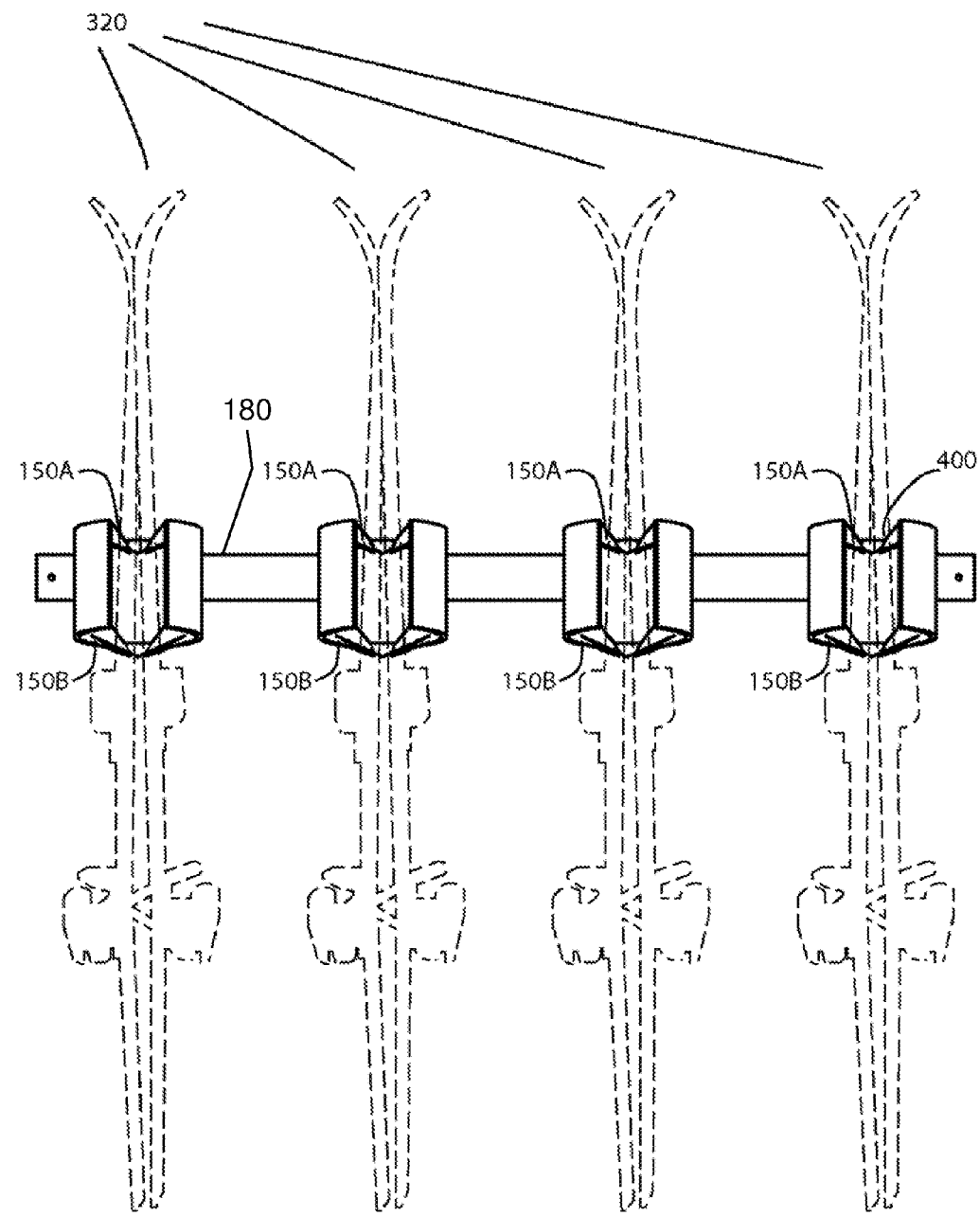
FIG. 12 shows yet another embodiment, holding a plurality of skis and configured to attach to a wall.
Figure 13A:
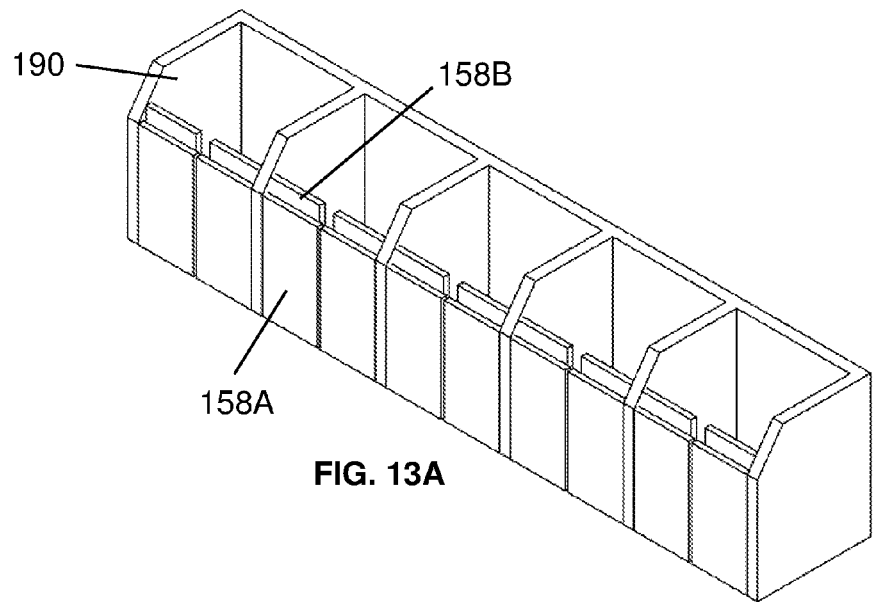
FIG. 13A shows another alternate configuration of a holder for structural long objects.
Figure 13B:
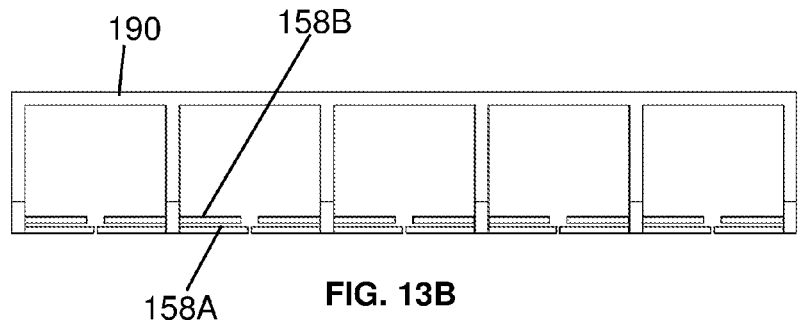
FIG. 13B is a top view of the holder of FIG. 12A.
Figure 13C:
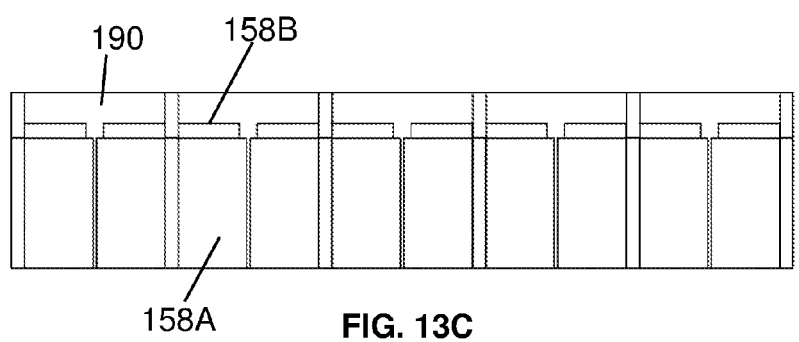
FIG. 13C is a front view of the holder of FIG. 12A.
Figures 15A, 15B, 15C:
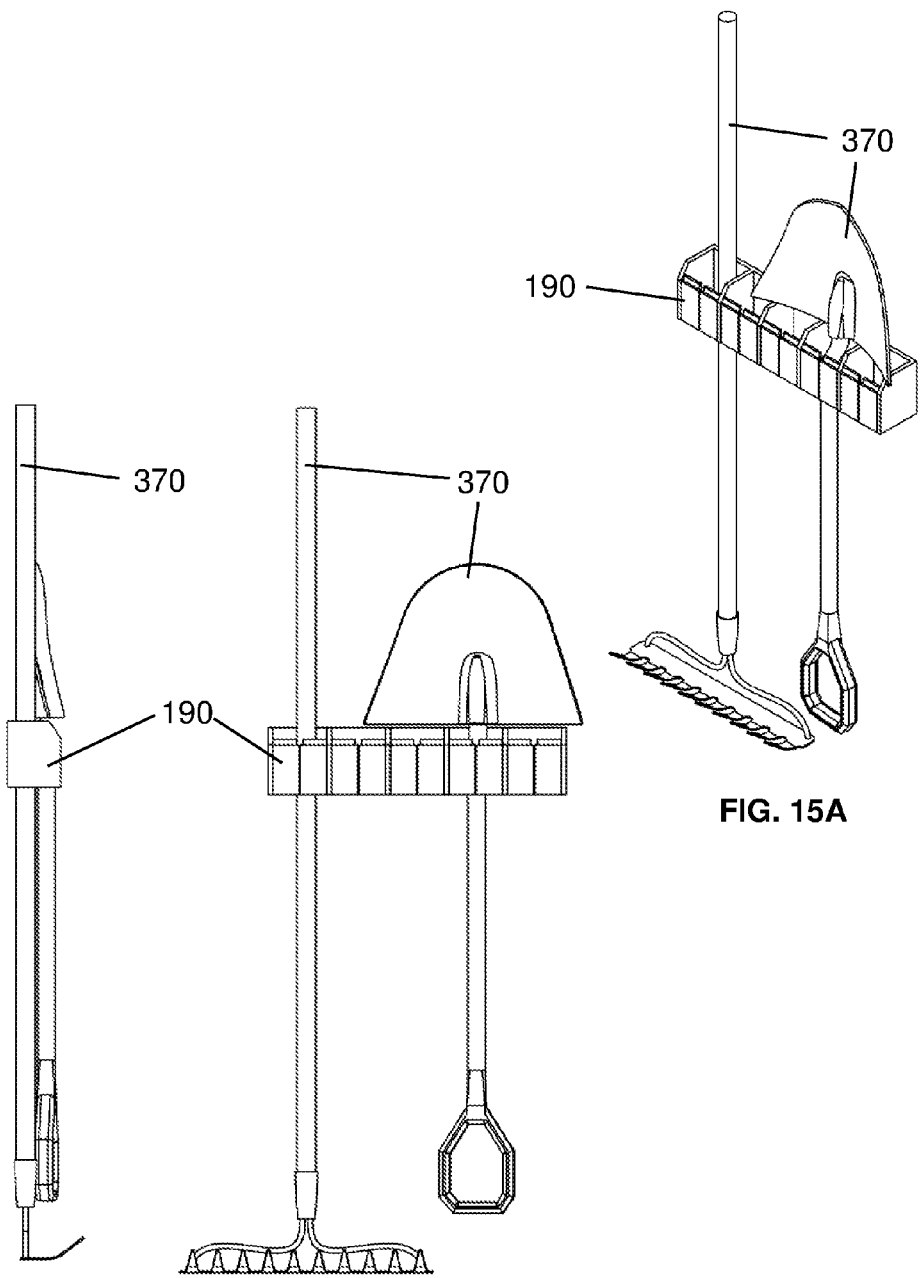
FIG. 15A shows the holder of FIG. 12A being used to hold garden tools.
FIG. 15B is a side view of the holder of FIG. 14A.
FIG. 15C is a front view of the holder of FIG. 14A.

As shown in FIG. 12, a user may displace a plurality of structural long objects such as skis 320 through the diaphragms 150A, 150B. In this embodiment of a holder 180, the long objects can be inserted at a midpoint along their lengths to vertically store the structural long objects. This holder embodiment 180, has an open perimeter 400 for each compartment, which allows for lateral insertion and engagement of the diaphragms. The embodiment shown in FIG. 12 could be mounted horizontally to a mobile or static structure.

Referring to FIG. 13A, FIG. 13B, FIG. 13C, FIG. 14A, FIG. 14B, FIG. 14C, FIG. 15A, FIG. 15B, and FIG. 15C, a multi-compartment multi-diaphragm holder 190 for structural long objects could also be constructed in a configuration using adjacent gate diaphragms, 158A and 158B, that create a "gate" to locate the structural long objects into the separate compartments. This configuration could be used for a variety of structural long objects including skis 320 and garden tools 370. Note that the diaphragms in this holding device 190 are substantially parallel to the intended direction of insertion of the structural long objects. This is different from the other embodiments shown in this enclosure, in which the diaphragms were substantially perpendicular to the intended direction of insertion of the structural long objects.

The foregoing description has been presented for purposes of illustration and description. Furthermore, the description is not intended to limit the inventions and/or aspects of the inventions to the forms disclosed herein. Consequently, variations and modifications commensurate with the above teachings, and skill and knowledge of the relevant art, are within the scope of the presented inventions. The embodiments described herein-above are further intended to explain best modes known of practicing the inventions and to enable others skilled in the art to utilize the inventions in such, or other embodiments and with various modifications required by the particular application(s) or use(s) of the presented inventions. It is intended that the appended claims be construed to include alternative embodiments to the extent permitted by the prior art.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The terms "coupled" and "linked" as used herein is defined as connected, although not necessarily directly and not necessarily mechanically. A device or structure that is "configured" in a certain way is configured in at least that way, but may also be configured in ways that are not listed. Also, the sequence of steps in a flow diagram or elements in the claims, even when preceded by a letter does not imply or require that sequence.

While the disclosure has been described with respect to a limited number of embodiments and areas of use, those skilled in the art, having benefit of this disclosure, will appreciate that other embodiments may be devised which do not depart from the scope of the disclosure as disclosed herein. The disclosure has been described in detail, it should be understood that various changes, substitutions and alterations could be made hereto without departing from the spirit and scope of the disclosure.

What is claimed is:

1. A device configured for holding a structural long object, wherein:

the device comprises:
   a body, further comprising a first lip;
   a first diaphragm stack, further comprising a first diaphragm and a second diaphragm; and
   a first retaining frame;
the first diaphragm comprises a first viscoelastic polymer;
the first diaphragm is flat in its rest state;
the first diaphragm is disposed over at least a portion of an aperture defined by the first lip;
the first diaphragm comprises a first plurality of intersecting slits comprising at least first and second slits extending through the thickness of the first diaphragm and outward toward the periphery of the first diaphragm, defining a first plurality of separable tabs in the first diaphragm;
the second diaphragm comprises a second viscoelastic polymer;
the second diaphragm is flat in its rest state;
the second diaphragm is in direct contact with the first diaphragm;
a flat plane of the second diaphragm is parallel to, adjacent to, and in contact with a flat plane of the first diaphragm when both the first diaphragm and the second diaphragm are in their rest states;
the second diaphragm comprises a second plurality of intersecting slits having at least first and second slits extending through the thickness of the second diaphragm and outward toward the periphery of the second diaphragm, defining a second plurality of separable tabs in the second diaphragm;
deflectable distal ends of the first plurality of separable tabs are configured to deflect in response to direct contact and deflection of deflectable distal ends of the second plurality of separable tabs in the direction of the first diaphragm;
deflectable distal ends of the second plurality of separable tabs are configured to deflect in response to direct contact and deflection of deflectable distal ends of the first plurality of separable tabs in the direction of the second diaphragm;
the first retaining frame is located on one side of the first diaphragm stack;
the first retaining frame is parallel to the flat plane of the first diaphragm and the flat plane of the second diaphragm when the first diaphragm and the second diaphragm are in their rest states;
the first lip is located on the side of the first diaphragm stack opposite of the first retaining frame;

the first lip is parallel to the flat plane of the first diaphragm and the flat plane of the second diaphragm when the first diaphragm and the second diaphragm are in their rest states;

the first retaining frame is configured for holding the first diaphragm stack against the first lip; and the first plurality of separable tabs and second plurality of separable tabs are configured for engaging the structural long object when the structural long object is being held by the device.

2. The device of claim 1, wherein:

the body comprises a second lip;

the device comprises a second diaphragm stack, further comprising a third diaphragm and a fourth diaphragm;

the device comprises a second retaining frame;

the third diaphragm comprises a third viscoelastic polymer;

the third diaphragm is flat in its rest state;

the third diaphragm is disposed over at least a portion of an aperture defined by the second lip;

the third diaphragm comprises a third plurality of intersecting slits comprising at least first and second slits extending through the thickness of the third diaphragm and outward toward the periphery of the third diaphragm, defining a third plurality of separable tabs in the third diaphragm;

the fourth diaphragm comprises a fourth viscoelastic polymer;

the fourth diaphragm is flat in its rest state;

the fourth diaphragm is adjacent to the third diaphragm on the side of the third diaphragm that is opposite the second lip;

the fourth diaphragm is in direct contact with the third diaphragm;

a flat plane of the fourth diaphragm is parallel to, adjacent to, and in contact with a flat plane of the third diaphragm when both the third diaphragm and the fourth diaphragm are in their rest states;

the fourth diaphragm comprises a fourth plurality of intersecting slits having at least first and second slits extending through the thickness of the fourth diaphragm and outward toward the periphery of the fourth diaphragm, defining a fourth plurality of separable tabs in the fourth diaphragm;

deflectable distal ends of the third plurality of separable tabs are configured to deflect in response to direct contact and deflection of deflectable distal ends of the fourth plurality of separable tabs in the direction of the third diaphragm;

deflectable distal ends of the fourth plurality of separable tabs are configured to deflect in response to direct contact and deflection of deflectable distal ends of the third plurality of separable tabs in the direction of the fourth diaphragm;

the second retaining frame is located on one side of the second diaphragm stack;

the second retaining frame is parallel to the flat plane of the third diaphragm and the flat plane of the fourth diaphragm when the third diaphragm and the fourth diaphragm are in their rest states;

the second lip is located on the side of the second diaphragm stack opposite of the second retaining frame;

the second lip is parallel to the flat plane of the third diaphragm and the flat plane of the fourth diaphragm when the third diaphragm and the fourth diaphragm are in their rest states;

the second retaining frame is configured for holding the second diaphragm stack against the second lip; and the third and fourth pluralities of separable tabs are configured for engaging the structural long object when the structural long object is being held by the device.

3. The device of claim 2, wherein:

the first diaphragm stack is oriented in a vertical plane;

the second diaphragm stack is oriented in a vertical plane that is parallel to the vertical plane of the first diaphragm stack; and the device is configured for horizontal storage of structural long objects.

4. The device of claim 2, wherein:

the body comprises an open top and a solid bottom;

the first diaphragm is rectangular in shape;

the second diaphragm is rectangular in shape;

the third diaphragm is rectangular in shape;

the fourth diaphragm is rectangular in shape;

the device further comprises a bottom pad;

the bottom pad is located inside the body adjacent to the solid bottom;

the bottom pad is rectangular in shape;

the bottom pad comprises a foam material;

the device is configured for simultaneously holding more than one structural long object;

the device is configured for holding structural long objects that comprise:
  a length that is at least four times greater than its width wherein the width is defined as a dimension perpendicular to the length;
  a thickness that is not greater than one fourth of the length wherein thickness is defined as a dimension orthogonal to the length; and
  a means for supporting themselves when aligned vertically in the length dimension.

5. The device of claim 1, wherein:

the first diaphragm stack further comprises an additional viscoelastic polymer diaphragm;

the additional diaphragm is flat in its rest state;

the additional diaphragm is adjacent to the second diaphragm on the side of the second diaphragm that is opposite the first diaphragm;

the additional diaphragm is in direct contact with the second diaphragm;

a flat plane of the additional diaphragm is parallel to, adjacent to, and in contact with a flat plane of the second diaphragm when both the second diaphragm and the additional diaphragm are in their rest states;

the additional diaphragm comprises an additional plurality of intersecting slits having at least first and second slits extending through the thickness of the additional diaphragm and outward toward the periphery of the additional diaphragm, defining an additional plurality of separable tabs in the additional diaphragm; and deflectable distal ends of the second plurality of separable tabs are configured to deflect in response to direct contact and deflection of deflectable distal ends of the additional plurality of separable tabs in the direction of the second diaphragm; and deflectable distal ends of the additional plurality of separable tabs are configured to deflect in response to direct contact and deflection of deflectable distal ends of the second plurality of separable tabs in the direction of the additional diaphragm.

6. The device of claim 1, wherein:

the first viscoelastic polymer is different from the second viscoelastic polymer.

7. The device of claim 6, wherein:
the first viscoelastic polymer comprises a chloroprene-based elastomer having a Shore A Durometer hardness between 40 and 50;
the first diaphragm is 1/16 inch thick;
the first diaphragm is rectangular;
the first plurality of separable tabs are blunt and rectangular;
the second viscoelastic polymer comprises rubber having a Shore A Durometer hardness between 40 and 50;
the second diaphragm is 1/16 inch thick;
the second diaphragm is rectangular;
the second plurality of separable tabs are pointed; and
tabs attached at opposite sides of the second diaphragm have their tips aligned.

8. The device of claim 1, wherein:
the first plurality of separable tabs have a different shape from the second plurality of separable tabs.

9. The device of claim 1, wherein:
the body comprises a plurality of compartments;
the first lip, first diaphragm stack, and first retaining frame are located in a first compartment;
the device comprises a second lip, second diaphragm stack, and second retaining frame located in a second compartment;
the second diaphragm stack comprises a third diaphragm and a fourth diaphragm;
the third diaphragm comprises a third viscoelastic polymer;
the third diaphragm is flat in its rest state;
the third diaphragm is disposed over at least a portion of an aperture defined by the second lip;
the third diaphragm comprises a third plurality of intersecting slits comprising at least first and second slits extending through the thickness of the third diaphragm and outward toward the periphery of the third diaphragm, defining a third plurality of separable tabs in the third diaphragm;
the fourth diaphragm comprises a fourth viscoelastic polymer;
the fourth diaphragm is flat in its rest state;
the fourth diaphragm is adjacent to the third diaphragm on the side of the third diaphragm that is opposite the second lip;
the fourth diaphragm is in direct contact with the third diaphragm;
a flat plane of the fourth diaphragm is parallel to, adjacent to, and in contact with a flat plane of the third diaphragm when both the third diaphragm and the fourth diaphragm are in their rest states;
the fourth diaphragm comprises a fourth plurality of intersecting slits having at least first and second slits extending through the thickness of the fourth diaphragm and outward toward the periphery of the fourth diaphragm, defining a fourth plurality of separable tabs in the fourth diaphragm;
deflectable distal ends of the third plurality of separable tabs are configured to deflect in response to direct contact and deflection of deflectable distal ends of the fourth plurality of separable tabs in the direction of the third diaphragm;
deflectable distal ends of the fourth plurality of separable tabs are configured to deflect in response to direct contact and deflection of deflectable distal ends of the third plurality of separable tabs in the direction of the fourth diaphragm;
the second retaining frame is located on one side of the second diaphragm stack;
the second retaining frame is parallel to the flat plane of the third diaphragm and parallel to the flat plane of the third diaphragm when the third diaphragm and the fourth diaphragm are in their rest states;
the second lip is parallel to the flat plane of the third diaphragm and parallel to the flat plane of the fourth diaphragm when the third diaphragm and the fourth diaphragm are in their rest states;
the second retaining frame is configured for holding the second diaphragm stack against the second lip; and
the third and fourth pluralities of separable tabs are configured for engaging a second structural long object when the second structural long object is being held by the device.

10. The device of claim 1, wherein:
the device is configured for vertically holding a plurality of objects in a configuration in which the objects do not touch each other;
the first plurality of separable tabs are aligned into two opposing rows;
the second plurality of separable tabs are aligned into two opposing rows;
the first viscoelastic polymer comprises the same material as the second viscoelastic polymer; and
the body is made of a plastic material.

11. A structural long object holding system comprising:
a housing further comprising an aperture and a first retaining feature;
a first stack of planar viscoelastic polymer sheets, further comprising a first sheet and a second sheet stacked directly on top of one another, wherein:
the first stack at least partially covers the aperture;
the first sheet comprises a first tab;
the second sheet comprises a second tab;
movement of a deflectable distal end of the first tab is responsive to direct contact and movement of a deflectable distal end of the second tab;
movement of the deflectable distal end of the second tab is responsive to direct contact and deflection of the deflectable distal end of the first tab;
the first retaining feature is parallel to a plane of the first sheet and a plane of the second sheet; and
a first attachment element that secures the first stack to the first retaining feature.

12. The system of claim 11, further comprising:
a second retaining feature located on the housing;
a second stack of planar viscoelastic polymer sheets, further comprising a third sheet and a fourth sheet stacked directly on top of one another, wherein:
the third sheet comprises a third tab;
the fourth sheet comprises a fourth tab;
movement of a deflectable distal end of the third tab is responsive to direct contact and movement of a deflectable distal end of the fourth tab;
movement of the deflectable distal end of the fourth tab is responsive to direct contact and deflection of the deflectable distal end of the third tab;
the second retaining feature is parallel to a plane of the third sheet and a plane of the fourth sheet; and
a second attachment element that secures the second stack to the second retaining feature.

13. The system of claim 11, wherein:
the first sheet and the second sheet are flat in their rest states;

the first sheet further comprises a first plurality of intersecting slits comprising at least first and second slits extending through the thickness of the first sheet and outward toward the periphery of the first sheet, defining a first plurality of separable tabs in the first sheet;

the second sheet further comprises a second plurality of intersecting slits having at least first and second slits extending through the thickness of the second sheet and outward toward the periphery of the second sheet, defining a second plurality of separable tabs in the second sheet;

movement of the deflectable distal ends of the first plurality of separable tabs are responsive to direct contact and movement of the deflectable distal ends of the second plurality of separable tabs;

movement of deflectable distal ends of the second plurality of separable tabs are responsive to direct contact and movement of deflectable distal ends of the first plurality of separable tabs;

the first retaining feature further comprises a first shelf;

the first attachment element further comprises a first frame wherein:
  the first frame is parallel to a plane of the first sheet and a plane of the second sheet;
  the first frame is located on the side of the first stack opposite the first shelf;
  the first retaining frame is configured for holding the first stack against the first shelf; and the first plurality of separable tabs and second plurality of separable tabs are configured for engaging the structural long object when the structural long object is being held by the system.

* * * * *